United States Patent [19]

Preciutti

[11] Patent Number: 4,920,992

[45] Date of Patent: May 1, 1990

[54] DENTAL FLOSSING APPARATUS

[76] Inventor: Roberto Preciutti, 5883 Cape Horn Dr., Agoura Hills, Calif. 91301

[21] Appl. No.: 410,424

[22] Filed: Sep. 21, 1989

[51] Int. Cl.$^5$ ............................................. A61C 15/00
[52] U.S. Cl. ..................................................... 132/323
[58] Field of Search ............... 132/323, 324, 325, 326, 132/327

[56] References Cited

U.S. PATENT DOCUMENTS

| | | | |
|---|---|---|---|
| 1,346,125 | 7/1920 | Hasbrook | 132/324 |
| 1,480,101 | 1/1924 | Ogden | 132/324 |
| 2,187,899 | 1/1940 | Henne | 132/323 |
| 2,837,098 | 6/1958 | Sorboro | 132/324 |
| 3,631,869 | 1/1972 | Espinosa | 132/323 |
| 3,847,168 | 11/1974 | Schlegel | 132/309 |
| 3,927,686 | 12/1975 | Zambito | 132/323 |

Primary Examiner—Gene Mancene
Assistant Examiner—Michael Lynch
Attorney, Agent, or Firm—Thomas I. Rozsa

[57] ABSTRACT

An improved dental flossing apparatus comprising a handle and a removable yoke member. The handle comprises an elongated shank for gripping purposes and a head piece having a receiving means for receiving a removable yoke and threads on the outer surface of the head surrounding the receiving means. In the preferred embodiment, the receiving means is an opening having a spherical cavity for receiving a spherical ball and a tapered throat area. The handle further comprises a slidable and threaded collar which can be slid onto and screwed around the opening to tighten the removable yoke to the handle. The yoke comprises two arms for retaining a length of dental floss between them and a stem terminating in sphere for insertion into the receiving means. The sphere provides a universal orientation for the yoke since the sphere can be rotated to any desired spherical rotation relative to the handle. Once the sphere is placed inside the receiving means such as the spherical cavity, the collar can be slid onto the threads on the outer surface of the head of the handle and threaded into place so that the stem and sphere of the yoke are firmly and safely held in place.

8 Claims, 1 Drawing Sheet

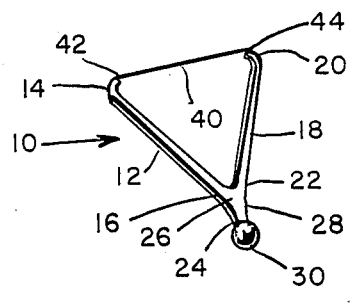
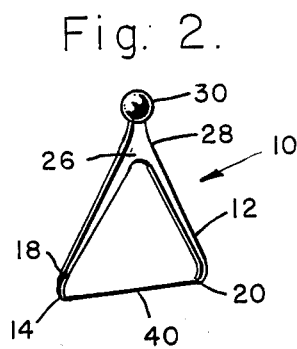
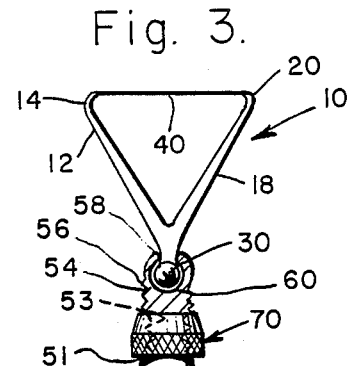
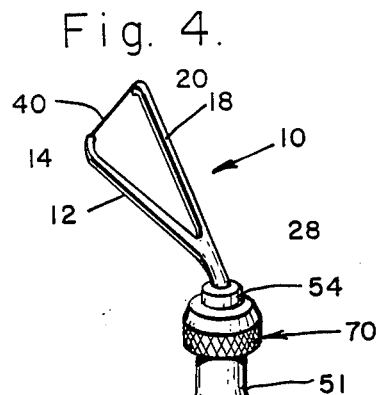
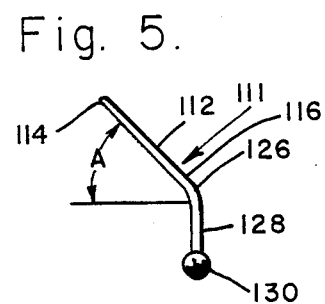
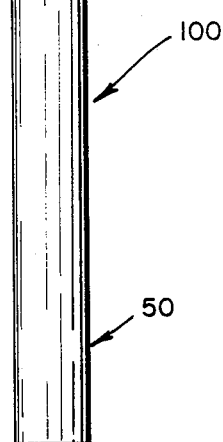
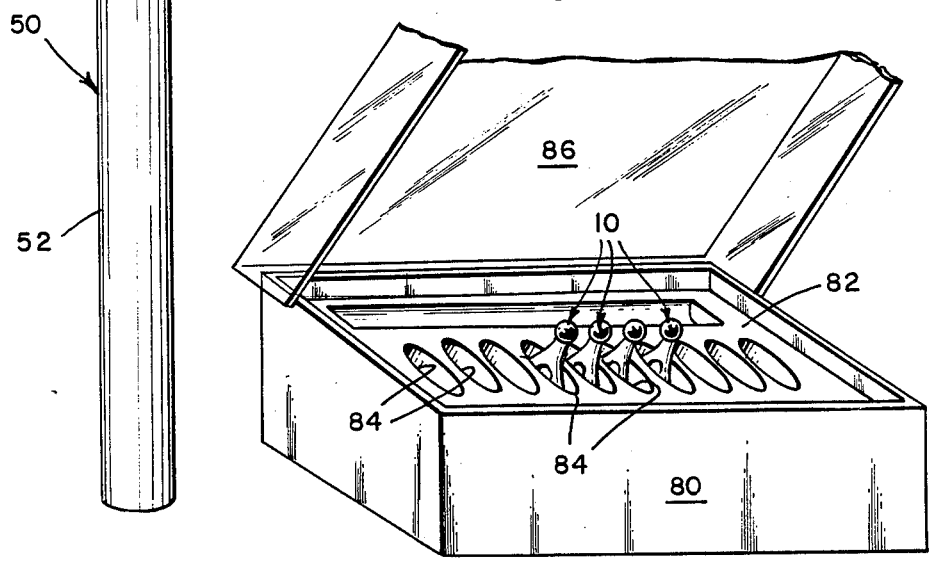

DENTAL FLOSSING APPARATUS

BACKGROUND OF THE INVENTION

1. Field of the Invention

The present invention relates to the field of dental floss which is a thread used to clean between teeth. More particularly, the present invention relates to the field of dental flossing apparatus which are designed to hold a length of dental floss in a given manner such that it can be used to clean the interstices between adjacent teeth.

2. Description of the Prior Art

In most conventional practice, an individual using dental floss to clean the interstices between the user's teeth unwraps a length of dental floss from its container and wraps one end of the floss around a finger of one hand and wraps the opposite end of the floss around a finger of the other hand and thereafter holds the length of floss taut between the two fingers so that it can be inserted between two adjacent teeth and moved back and forth to clean the area. One problem with this method is that a large amount of floss is used. Second, it is sometimes difficult to reach back areas of the mouth when holding the length of floss in this manner.

In some instances, attempts have been made to provide devices for holding the length of floss, which usually takes the form of a yoke across which a portion of the floss is trained while the opposite ends are wrapped about the projecting legs of the yoke. The entire apparatus is then placed in the user's mouth while the fingers manipulate the device between the teeth for cleansing. Several prior art patents disclose variations on this concept. They are as follows:

1. U.S. Pat. No. 3,927,686 issued in 1975 to Zambito for "Dental Floss Holder".
2. U.S. Pat. No. 3,631,869 issued in 1972 to Espinosa for "Dental Floss Holder".
3. U.S. Pat. No. 3,847,168 issued in 1974 to Schlegel for "Tooth Cleaning Appliance".
4. U.S. Pat. No. 2,837,098 issued in 1958 to Sorboro for "Dental Floss Holder And Dispenser".
5. U.S. Pat. No. 1,480,101 issued in 1924 to Ogden for "Dental Floss Appliance".
6. U.S. Pat. No. 2,187,899 issued in 1940 to Henne for "Dental Floss Throw-Away Unit".
7. U.S. Pat. No. 1,346,125 issued in 1982 to Hasbrook for "Sanitary Teeth Cleaner".
8. U.S. Pat. No. 4,319,595 issued in 1982 to Ulrich for "Dental Care Unit".

The apparatus disclosed in Zambito has several disadvantages. Besides being expensive to manufacture, the method of attaching the head holding the floss to the handle cannot provide a firm and secure grip on the head. As a result, when used with vigorous action as is common when flossing, it is possible for the head to come loose and fall into the user's throat and cause the user to choke. In addition, the device does not provide a universal choice of positioning the head orientation and therefore certain parts of the mouth such as the back teeth may be difficult to reach and clean with this device. Further, Zambito does not provide a choice of flossing means and it is also vitally important to prevent sagging of the floss itself.

The apparatus disclosed in Espinosa also has several problems. Not enough tension can possibly be applied to the floss by this method. During flossing, the floss would sag and make the floss device useless. As with the device in Zambito, the device does not provide a universal choice of positioning the head orientation and therefore certain parts of the mouth such as the back teeth may be difficult to reach and clean with this device. In addition, this device with its many grooves, channels, indentations and other slot attachments is an expensive device to manufacture.

The apparatus disclosed in Schlegel is also an expensive and cumbersome device to manufacture and further has a complicated way for retaining the floss. The floss can easily become loose and sag making it worthless for flossing. In addition, the yoke has only one orientation, making it difficult to reach certain parts of the mouth.

The apparatus disclosed in Sorboro, Ogden, Henne, and Hasbrook also have many of the disadvantages previously discussed. The yoke holding the floss is once again in a fixed orientation making it difficult to reach certain parts of the mouth. The complicated structure is also expensive to manufacture.

The apparatus in Ulrich is a dental water pik.

Overall, the prior art embodiments of yoke apparatus which retain a length of dental floss all have in common one or more of the following defects. First, the yoke is oriented in a fixed position and cannot be adjusted to accommodate difficult locations in the mouth. Second, the device is complicated and expensive to manufacture. Third, the floss itself is not held securely and can easily sag and come loose during use, thereby making it worthless. Therefore, there is a significant need for a flossing apparatus which overcomes these defects.

SUMMARY OF THE PRESENT INVENTION

The present invention relates to an improved dental flossing apparatus comprising a handle and a removable yoke member. The handle comprises an elongated shank for gripping purposes and a head piece having a receiving means for receiving a removable yoke and threads on the outer surface of the head surrounding the receiving means. In the preferred embodiment, the receiving means is an opening extending into a spherical cavity for receiving a spherical ball and a tapered throat section. The handle further comprises a slidable and threaded collar which can be slid onto and screwed around the opening to tighten the removable yoke to the handle. The yoke comprises two arms for retaining a length of dental floss between them and a stem terminating in a sphere for insertion into the receiving means. The sphere provides a universal orientation for the yoke since the sphere can be rotated to any desired spherical rotation relative to the handle. Once the sphere is placed inside the receiving means such as the spherical cavity, the collar can be slid onto the threads on the outer surface of the head of the handle and threaded into place so that the stem and sphere of the yoke are firmly held in place. In this way, the yoke can be retained securely within the handle so that it cannot possibly fall out and fall into a user's throat during use and at the same time can be oriented at any desired angle to accommodate different locations in the user's mouth. The portion of floss is retained between the yokes by being bonded to the tips of the arms of the yoke so that it cannot come loose or sag during use.

It has been discovered, according to the present invention, that if a yoke used to retain a section of dental floss between the tips of the arms of the yoke has a stem terminating in a sphere, then the stem and sphere can be inserted into a receiving cavity of a handle and oriented at any desired orientation relative to the handle so that any desired location of the mouth can be reached.

It has further been discovered, according to the present invention that if the handle comprises a spherical cavity for receiving the stem and sphere of the yoke and the handle further comprises a slidable collar which contains securing means for tightening the yoke onto the handle, then the removable yoke can be securely tightened onto the collar to prevent it coming loose during flossing.

It has additionally been discovered that if a container comprises an elongated slot, a multiplicity of yoke members can be retained therein in a sanitary manner. The slot comprises a multiplicity of oval openings for receiving a respective one of the yokes. The retaining means can also comprise an openable top so that the user can select a given yoke for use while the remaining yokes are saved for future use.

It is therefore an object of the present invention to provide a dental flossing apparatus wherein the yoke retaining the dental floss can be orientated at any desired angle relative to the handle retaining the yoke so that the yoke can reach any desired portion of the mouth.

It is another object of the present invention to provide a dental flossing apparatus wherein a removable yoke is securely retained on the handle during use so that the yoke cannot come loose during use and accidentally fall into the user's throat.

It is a further object of the present invention to provide a retaining means for retaining a multiplicity of yokes so that a yoke and its floss can be used and thereafter discarded and the remaining yokes can be retained in a sanitary manner until their use is required.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is a front elevational view of the removable yoke of the present invention, illustrating a length of dental floss retained between the tips of the arms of the yoke.

FIG. 2 is a perspective view of the removable yoke of the present invention, oriented in a downwardly facing direction.

FIG. 3 is a front elevational view in partial cross-section, illustrating the present invention dental flossing apparatus, with the slidable collar slid down away from the head of the handle and the connection area illustrated in cross-section to show how the stem and sphere of the yoke fit within the cavity in the head of the handle.

FIG. 4 is a perspective view of the present invention dental flossing apparatus, with the slidable collar in its retaining position to securely retain the yoke on the handle.

FIG. 5 is a side view of a case to retain multiplicity of removable yokes, showing some of the yokes retained therein.

FIG. 6 is a perspective view of a container for the yokes, illustrating some yokes retained therein.

DETAILED DESCRIPTION OF THE PREFERRED EMBODIMENT

Although specific embodiments of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

Referring particularly to FIG. 1, there is illustrated at 10 the preferred embodiment of the removable yoke of the present invention. The removable yoke 10 comprises a pair of arms 12 and 18. Arm 12 is set at a vertical angle and terminates in a rounded tip 14 at its upper end. The lower end 16 of arm 12 is formed into the yoke base 26. Arm 18 is set at a vertical angle and terminates in a rounded tip 20 at its upper end. The lower end 22 of arm 18 is formed into the yoke base 26. The two arms 12 and 18 extend away from each other to form a generally "V" shaped configuration. The stem 28 is formed into and extends downwardly from the base. As illustrated in FIG. 2, the arms 12 and 18 and the stem 28 are aligned in the same vertical plane. The lower tip 24 of stem 28 is affixed to a sphere 30. While the portions of the yoke have been individually described, it will be appreciated that the entire removable yoke 10 is made out of one piece construction and the arms 12 and 18, base 26, stem 28 and sphere 30 are all molded out of one piece and preferably made out of a molded plastic material.

Stretched across the interior upper area of the yoke 10 is a piece of dental floss 40. End 42 of dental floss 40 is bonded to the rounded tip 14 of arm 12. End 44 of dental floss 40 is bonded to the rounded tip 20 of arm 18. The bonding means may be glue or other suitable adhesive which serves to bond the thread 40 to the tips of the arms of the yoke. Alternatively, a process can be provided wherein the length of dental floss is directly bonded to the tips as the yoke is being molded. In this way, the dental floss 40 is held taut between the tips of the arms of the yoke and therefore cannot come loose and will not sag during use.

The handle member 50 of the present invention dental flossing apparatus is illustrated in FIG. 3. The handle 50 comprises an elongated shank portion 52 and a head section 54. The head section 54 further comprises threads 56 on its exterior surface. The upper portion of the head section 54 further comprises an internal opening 58 which terminates in an internal spherical cavity 60. The internal opening 58 is narrower than the spherical cavity 60. As illustrated in FIG. 3, the yoke 10 is inserted into the internal opening 58 such that the sphere 30 rests within the spherical cavity 60 while the stem 28 extends through the internal opening 58 such that the base 26 and arms 12 and 18 rest above the head 54. It will be appreciated that the angle orientation of the base 26 and arms 12 and 18 relative to the head 54 can be at any desired angle since the sphere 30 can be rotated within the spherical cavity 60 to any desired relative spherical orientation. It has been experimentally determined that the preferred relative angle of the arms of the yoke to the head section of the handle is approximately 30 degrees, but any suitable range of angles such as 15 degrees to 75 degrees can be effective, depending on the individual user's mouth and the specific teeth to be reached.

The handle 50 also comprises a slidable collar 70. The physical structure of the handle comprises an elongated stem 52 extending into a throat area 51 which in turn extends into the head section 54. The slidable collar 70 can be slid down around the throat area 51 when the handle 50 is not in use and when it is desired to insert a removable yoke 10. After the yoke 10 is placed into the head section as previously described, the slidable collar 70 is then slid up onto the head section. The internal surface of the slidable collar 70 has a multiplicity of threads 53 and are designed for threaded mating engagement with the threads 56 on the outer surface of the head. As the collar 70 is tightened around the head section 54, the stem 26 and sphere 30 are securely retained within the head section and the angle orientation which was set before the tightening began. Therefore, through this apparatus, the yoke 10 can be securely tightened onto the head section 54 of handle 50. The complete dental flossing apparatus 100 is illustrated in FIG. 4 with a yoke securely affixed to the handle. The user holds the dental flossing apparatus 100 by the handle 50 and inserts the yoke 10 into his mouth and inserts the taut dental floss 40 into a location between adjacent teeth to thereby clean the area by moving the handle and therefore the dental floss back and forth. After the entire teeth flossing operation has been completed, the yoke with the used dental floss can be removed from the handle 50 by rotating the threaded collar 70 in the opposite direction to untighten it and have it slide back onto the throat area 51 of handle 50. The yoke 10 can thereafter be easily removed and on subsequent flossing uses, a new fresh yoke with fresh dental floss can be inserted into the head section of the handle.

A multiplicity of yokes 10 can be retained through a simple and efficient case arrangement as illustrated in FIG. 6. The case 80 comprises a horizontal surface 82 which in turn comprises a multiplicity of openings 84 aligned in a row. By way of example, the openings can be generally oval shaped and sized so that the length of the opening is just long enough to accommodate the tips 14 and 20 of the arms 12 and 18 respectively of the yoke 10. As illustrated in FIG. 5, the yoke 10 is inserted into the oval opening such that the yoke 10 faces downwardly and the taut dental floss 40 is protected from dirt and debris. A cover 86 can be used to protect the group of yokes. The yokes can be sold in a package format which by way of example is a cellophane wrapping and the package is opened and a respective yoke is inserted into a respective opening 84 in surface 82 of case 80.

An alternative embodiment of the yoke 111 is illustrated in FIG. 5. The removable yoke 111 comprises a pair of arms, 112 and a second arm not shown comparable to arm 18 in FIG. 1. Arm 112 is set at a vertical angle and terminates in a rounded tip 114 at its upper end. The lower end 116 of arm 112 is formed into the yoke base 126. The second arm is also set at a vertical angle and terminates in a rounded tip at its upper end. The lower end of the second arm is also formed into the yoke base 126. The two arms extend away from each other to form a generally "V" shaped configuration. The stem 128 is formed into an extends downwardly from the base 126. The lower tip of stem 128 is affixed to a sphere 130. While the portions of the yoke have been individually described, it will be appreciated that the entire removable yoke 111 is made out of one piece construction and the arms, base, stem and sphere are all molded out of one piece and preferably made out of a molded plastic material.

Stretched across the interior upper area of the yoke 111 is a piece of dental floss in the manner previously described for yoke 10.

All of the elements of this alternative embodiment yoke 111 are the same as the embodiment illustrated in FIG. 1 with the one difference being that the base 126 and arms 112 (and the second arm not shown) are offset at an angle "A" relative to the stem 128. In the preferred embodiment, the angle "A" is approximately 30 degrees but other angles in the range of 15 degrees to 75 degrees are also within the spirit and scope of the present invention. With the yoke 111 offset at this given angle, the relative orientation of the yoke 111 to the handle 50 and its head 54 is set and it only need be rotated as desired. The manner of insertion of stem 128 and sphere 130 into opening 58 and spherical cavity 60 is identical to the manner previously described for stem 28 and sphere 30 of yoke 10.

Therefore, through use of the present invention, the user can safely floss all of his/her teeth, discard the used yoke, and quickly and efficiently replace it with a new fresh yoke containing new fresh dental floss. The yoke 10 or 111 is safely retained within the head section 54 of handle 50 in a secure manner to assure that the yoke will not accidentally fall out during use and cannot cause possible injury such as becoming embedded in the user's throat. Through use of the present invention, the yoke can be oriented to any desired angle and oriented relative to the handle so that all areas of the user's mouth can be reached.

Therefore, the present invention can be defined as a dental flossing apparatus comprising:
a. a handle member further comprising,
   (i) an elongated shank,
   (ii) a throat section extending from the elongated shank and extending to a head section,
   (iii) the head section including an internal opening at the top of the head section leading to an internal spherical cavity, the outer surface of the head section having threads thereon,
   (iv) a slidable collar which rests around the throat area of the head section and having internal threads for mating engagement with the threads on the head section;
b. a removable yoke further comprising,
   (i) a first arm having a rounded upper tip,
   (ii) a second arm having a rounded upper tip,
   (iii) a base,
   (iv) the first and second arms joined to the base of the yoke at their lower ends and extending away from each other to form a V-shape with their respective upper tips at the top of the V shape,
   (v) a stem extending from the base in a direction away from the first and second arm,
   (vi) a sphere attached at the remote end of the stem, and
   (vii) a length of dental floss bonded to the rounded tips of the yoke so that the length of dental floss is stretched taut between the tips of the yoke;
c. whereby the stem and sphere of the yoke are removably inserted into the opening in the head of the handle such that the sphere rests within the spherical cavity and the yoke is oriented at any angle relative to the head and and handle and the collar is threaded onto the head to securely engage the yoke to the head.

Defined more broadly, the present invention is defined as a dental flossing apparatus comprising:
a. a handle including a grasping section for holding the handle and a head section;
b. a yoke member retaining a taut length of dental floss thereon, the yoke member having engaging means for removable engagement with said head second;
c. said head including means for retaining said yoke in a removable manner;
d. said yoke having orientation means for orienting the yoke at any desired orientation relative to said head section after insertion into the retaining means of the head section; and
e. engagement means on said head section for retaining the yoke in a fixed position after it has been inserted into the head section and aligned at the desired relative orientation.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus is intended only for illustration and for disclosure of an operative embodiment and not to show all of the various forms or modification in which the invention might be embodied or operated.

The invention has been described in considerable detail in order to comply with the patent laws by providing full public disclosure of at least one of its forms. However, such detailed description is not intended in any way to limit the broad features or principles of the invention, or the scope of patent monopoly to be granted.

What is claimed is:
1. A dental flossing apparatus comprising:
a. a handle member further comprising,
   (i) an elongated shank,
   (ii) a throat section extending from the elongated shank and extending to a head section,
   (iii) the head section including an internal opening at the top of the head section leading to an internal spherical cavity, the outer surface of the head section having threads thereon,
   (iv) a slidable collar which rests around the throat area of the head section and having internal threads for mating engagement with the threads on the head section;
b. a removable yoke further comprising,
   (i) a first arm having a rounded upper tip,
   (ii) a second arm having a rounded upper tip,
   (iii) a base,
   (iv) the first and second arms joined to the base of the yoke at their lower ends and extending away from each other to form a V-shape with their respective upper tips at the top of the V shape,
   (v) a stem extending from the base in a direction away from the first and second arm,
   (vi) a sphere attached at the remote end of the stem, and
   (vii) a length of dental floss bonded to the rounded tips of the yoke so that the length of dental floss is stretched taut between the tips of the yoke;
c. whereby the stem and sphere of the yoke are removably inserted into the opening in the head of the handle such that the sphere rests within the spherical cavity and the yoke is oriented at any angle relative to the head and and handle and the collar is threaded onto the head to securely engage the yoke to the head.

2. A dental flossing apparatus in accordance with claim 1 wherein said first and said second arm are offset at an angle relative to said stem of said yoke.

3. A dental flossing apparatus in accordance with claim 2 wherein said angle is approximately 30 degrees.

4. A dental flossing apparatus in accordance with claim 1 further comprising a retaining container having openings to retain a multiplicity of individual yokes with the tips of the arms of each yoke retained within a surface of the container to shield the dental floss and the stem of each yoke extending upwardly from the retaining surface.

5. A dental flossing apparatus comprising:
a. a handle member further comprising,
   (i) an elongated shank,
   (ii) a throat section extending from the elongated shank and extending to a head section,
   (iii) the head section including an internal opening at the top of the head section leading to an internal spherical cavity,
   (iv) a slidable collar which rests around the throat area of the head section and having means for engaging the collar and tightening it about the head section;
b. a removable yoke further comprising,
   (i) a first arm having an upper tip,
   (ii) a second arm having a, upper tip,
   (iii) a base,
   (iv) the first and second arms joined to the base of the yoke at their lower ends and extending away from each other to form a V-shape with their respective upper tips at the top of the V shape,
   (v) a stem extending from the base in a direction away from the first and second arm,
   (vi) a sphere attached at the remote end of the stem, and
   (vii) a length of dental floss bonded to the tips of the yoke so that the length of dental floss is stretched taut between the tips of the yoke;
c. whereby the stem and sphere of the yoke are removably inserted into the opening in the head of the handle such that the sphere rests within the spherical cavity and the yoke is oriented at any angle relative to the head and and handle, and the collar is tightened about the head section to securely engage the yoke to the head.

6. A dental flossing apparatus in accordance with claim 5 wherein said first and said second arm are offset at an angle relative to said stem of said yoke.

7. A dental flossing apparatus in accordance with claim 6 wherein said angle is approximately 30 degrees.

8. A dental flossing apparatus in accordance with claim 5 further comprising a retaining container having openings to retain a multiplicity of individual yokes with the tips of the arms of each yoke retained within a surface of the container to shield the dental floss and the stem of each yoke extending upwardly from the retaining surface.

* * * * *